United States Patent [19]

Schlosser et al.

[11] Patent Number: 5,550,236
[45] Date of Patent: Aug. 27, 1996

[54] PROCESS FOR CROSS-COUPLING AROMATIC BORONIC ACIDS WITH AROMATIC HALOGEN COMPOUNDS OR PERFLUOROALKYLSULFONATES

[75] Inventors: Hubert Schlosser, Glashütten/Taunus; Rainer Wingen, Hattersheim/Main; Javier Manero, Frankfurt am Main, all of Germany

[73] Assignee: Hoechst Aktiengesellschaft, Frankfurt, Germany

[21] Appl. No.: 424,254

[22] PCT Filed: Oct. 6, 1993

[86] PCT No.: PCT/EP93/02733

§ 371 Date: Apr. 24, 1995

§ 102(e) Date: Apr. 24, 1995

[87] PCT Pub. No.: WO94/10105

PCT Pub. Date: May 11, 1994

[30] Foreign Application Priority Data

Oct. 26, 1992 [DE] Germany .......................... 42 36 103.6

[51] Int. Cl.$^6$ ...................... C07D 213/26; C07D 239/30; C07D 401/04; C07D 403/04

[52] U.S. Cl. .......................... 544/238; 544/333; 544/334; 544/335; 544/409; 544/316; 544/224; 544/405; 544/315; 544/242; 544/410; 544/360; 544/364; 544/395; 544/403; 546/339; 546/345; 546/302; 546/303; 546/261; 546/239; 546/259; 546/268.7; 546/286; 546/290; 546/346; 546/192; 546/269.7; 546/193; 546/194; 558/357; 560/102; 564/181; 568/437; 568/642; 570/143; 570/182; 570/190; 548/239

[58] Field of Search .................... 544/238, 333, 544/334, 335, 310, 409; 546/339, 345, 302, 303, 261, 275, 239, 259

[56] References Cited

U.S. PATENT DOCUMENTS 5,254,776  10/1993  Lang et al. ............................ 570/190

FOREIGN PATENT DOCUMENTS

3930663C1  9/1989  Germany .
WO89/12039  12/1989  WIPO .

OTHER PUBLICATIONS

Ali, Naji M., et al., "Palladium–Catalysed Cross–Coupling Reactions of Arylboronic Acids with π–Deficient Heteroaryl Chlorides[+1]" Tetrahedron, 48, No. 37, pp. 8117–8126, 1992. Month of publication not provided.

Primary Examiner—Mukund J. Shah
Assistant Examiner—King Lit Wong
Attorney, Agent, or Firm—Curtis, Morris & Safford, P.C.

[57] ABSTRACT

A process for preparing polycyclic aromatic compounds by cross-coupling aromatic boronic acids with aromatic halogen compounds or perfluoroalkylsulfonates in the presence of metallic palladium, if desired applied to a support material, as catalyst, wherein the coupling is carried out in the presence of a ligand and a base. The process of the invention allows the yield of polycyclic aromatic compounds to be significantly increased in comparison with processes not using a ligand and thus allows a yield optimum for the Pd(0)-catalyzed cross-coupling of aromatic boronic acids with aromatic halogen compounds to be achieved.

8 Claims, No Drawings

PROCESS FOR CROSS-COUPLING AROMATIC BORONIC ACIDS WITH AROMATIC HALOGEN COMPOUNDS OR PERFLUOROALKYLSULFONATES

The invention relates to a process for preparing polycyclic aromatic compounds by cross-coupling aromatic boronic acids with aromatic halogen compounds or perfluoroalkylsulfonates catalyzed by metallic palladium, if desired applied to a support material.

The palladium-catalyzed cross-coupling reaction of terminal alkynes and organometallic alkyl, alkenyl, allyl or aryl compounds with alkyl, alkenyl, allyl or aryl halides or sulfonates has been utilized to an increasing extent in many areas of organic synthesis for some years (see, for example B. M. Trost, T. R. Verhoeven in: Comprehensive Organometallic Chemistry Volume 8, p. 779 ff., Pergamon Press, Oxford 19 . . . ).

The cross-coupling of metallated aryls with aromatic halides has been carried out, for example, using Grignard and organolithium reagents (see, for example, J.-F. Fauvarque and A. Jutard, Bull. Chim. Soc. Fr., 1976, 765, A. Sekiya and N. Ishikawa, J. Organomet. Chem., 1976, 118, 349, A. Sekija and N. Ishikawa, J. Organomet. Chem., 1977, 125, 281, M. Yamamura, I. Moritani and S. I. Murahashi, J. Organomet. Chem., 1975, 91, C39, S. I. Murahashi, M. Yamamura, K. Yanagiswa, N. Mira and K. Kondo, J. Org. Chem., 1979, 44, 2408, A. Minato, K. Tamao, T. Hayashi, K. Suzuki and M. Kumada, Tetrahedron Lett., 1980, 845.), organozinc reagents (for example, E. Negishi et al. J. Org. Chem. 42 (1977) 1822. ) and organotin reagents (for example, M. Kosogi et al., Chem. Lett. 1977, 301.).

Aromatic boron compounds too, such as boronic acids and their derivatives or boranes, have already been used for coupling with aromatic halogen compounds or perfluoroalkylsulfonates (see, for example, B. N. Miyaura, T. Yanagi, A. Suzuki in Synthetic Communications 11 (1981), p. 513 ff.; M. J. Sharp, W. Cheng, V. Snieckus in Tetrahedron Letters 28 (1987), p. 5093 ff.; G. W. Gray in J. Chem. Soc. Perkin Trans II, 1989, p. 2041 ff. and Mol. Cryst, Sig. Cryst, 172 (1989), p. 165 ff., 204 (1991), p. 43 ff and p. 91 ff.; EP 0 449 015; WO 89/12039; WO 89/03821; EP 0 354 434).

All these processes are homogeneously catalyzed processes using Pd(0) complexes, in particular tetrakis(triphenylphosphine)palladium(0).

However, the disadvantage of these processes is clearly in the high catalyst costs which make difficult the economical transfer of the processes to a larger production scale (kg, t). The homogeneous reaction procedure furthermore makes difficult an efficient regeneration of the palladium catalyst and can easily lead to contamination of the waste formed in the reaction with palladium.

For this reason, processes have been developed which circumvent these problems by heterogeneous use of the catalyst. EP-A-0 152 450 describes the coupling of Grignard reagents under heterogeneous Pd(0) catalysis. However, owing to the high reactivity of the organomagnesium component, the selection of starting materials for this process is severely limited. The German Patent 3 930 663 describes a process for preparing liquid-crystalline compounds in which halides and organometallic compounds, including boronic acids, are reacted in inert solvents using metallic palladium, if desired applied to a support material, as catalyst, if desired in the presence of a metal alkoxide. Although this procedure can substantially reduce the catalyst costs and the palladium can easily be regenerated after the reactions are complete, this process often gives the desired coupling product in only unsatisfactory yields.

It is therefore an object of the present invention to find a process for coupling aromatic boronic acids with aromatic halogen compounds or perfluoroalkylsulfonates, which process does not have the disadvantages described for the previous processes.

It has surprisingly been found that in the reaction of aromatic boronic acids with aromatic halogen compounds or perfluoroalkylsulfonates in the presence of a base and catalytic amounts of metallic palladium, if desired applied to a support material, excellent yields of polycyclic aromatic compounds can be obtained by addition of catalytic amounts of a ligand.

The invention accordingly provides a process for preparing polycyclic aromatic compounds by cross-coupling aromatic boronic acids with aromatic halogen compounds or perfluoroalkylsulfonates in the presence of metallic palladium, if desired applied to a support material, as catalyst, wherein the coupling is carried out in the presence of a ligand and a base.

The coupling reaction proceeds chemoselectively, so that even electrophilic groups such as esters or nitriles do not impair the course of the reaction.

The catalyst system used in this process, comprising metallic palladium, if desired applied to a support material, and a ligand, is derived from components which are commercially available at low cost and which allow economical operation of the process. In addition, the palladium metal obtained as a solid after the reaction is complete can be easily separated off, regenerated and recycled to the catalyst process, which achieves an additional lowering of the process costs and avoids contamination of the waste products by palladium.

The addition according to the invention of catalytic amounts of a ligand allows the yield of polycyclic aromatic compounds to be significantly increased in comparison with processes not using a ligand and thus allows a yield optimum for the Pd(0)-catalyzed cross-coupling of aromatic boronic acids with aromatic halogen compounds to be achieved.

To carry out the process of the invention, the aromatic boronic acid, the aromatic halogen compound or the perfluoroalkylsulfonate, the base, the catalytic amount of metallic palladium, if desired applied to a support material, and the catalytic amount of a ligand are preferably added to an inert solvent or inert solvent mixture and stirred at a temperature of from 0° C. to 200° C., preferably at from 30° C. to 170° C., particularly preferably at from 50° C. to 150° C., most particularly preferably at from 60° to 120° C., for a period of from 1 hour to 100 hours, preferably from 5 hours to 70 hours, particularly preferably from 10 hours to 50 hours, most particularly preferably from 15 hours to 30 hours. After the reaction is complete, the Pd catalyst obtained as solid is separated off by filtration, the crude product is freed of the solvent or the solvents and is subsequently purified by methods known to those skilled in the art and matched to the respective product, e.g. by recrystallization, distillation, sublimation, zone melting, melt crystallization or chromatography.

Solvents suitable for the process of the invention are, for example, ethers, e.g. diethyl ether, dimethoxymethane, diethylene glycol dimethyl ether, tetrahydrofuran, dioxane, diisopropyl ether, tert-butyl methyl ether, hydrocarbons, e.g. hexane, iso-hexane, heptane, cyclohexane, benzene, toluene, xylene, alcohols, e.g. methanol, ethanol, 1-propanol, 2-propanol, ethylene glycol, 1-butanol, 2-butanol, tert-butanol, ketones, e.g. acetone, ethyl methyl ketone, iso-butyl methyl ketone, amides, e.g. dimethylformamide, dimethylacetamide, N-methylpyrrolidone, nitriles, e.g. acetonitrile, propionitrile, butyronitrile, water and mixtures of the same.

Preferred solvents are ethers such as dimethoxyethane, diethylene glycol dimethyl ether, tetrahydrofuran, dioxane, diisopropyl ether, hydrocarbons such as hexane, heptane, cyclohexane, benzene, toluene, xylene, alcohols such as methanol, ethanol, 1-propanol, 2-propanol, 1-butanol, 2-butanol, ethylene glycol, ketones such as ethyl methyl ketone, iso-butyl methyl ketone, amides such as dimethylformamide, dimethylacetamide, N-methylpyrrolidone, hexamethylphosphoramide, water and mixtures of the same.

Particularly preferred solvents are ethers, e.g. dimethoxyethane, tetrahydrofuran, hydrocarbons, e.g. cyclohexane, benzene, toluene, xylene, alcohols, e.g. ethanol, 1-propanol, 2-propanol, water and mixtures of the same.

Most particularly preferred are dimethoxyethane, benzene, toluene, ethanol, water and mixtures of the same.

Bases which are preferably used in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, and also primary, secondary and tertiary amines.

Particularly preferred are alkali metal and alkaline earth metal hydroxides, alkali metal and alkaline earth metal carbonates and alkali metal hydrogen carbonates. Most particularly preferred are alkali metal hydroxides, alkali metal carbonates and alkali metal hydrogen carbonates, such as lithium carbonate, sodium carbonate, potassium carbonate.

The base is preferably used in the process of the invention in a proportion of from 100 to 1000 mol %, particularly preferably from 100 to 500 mol %, very particularly preferably from 150 to 400 mol %, in particular from 180 to 250 mol %, based on the aromatic boronic acid.

The catalyst used is metallic palladium, preferably palladium in powdered form or on a support material, e.g. palladium on activated carbon, palladium on aluminum oxide, palladium on barium carbonate, palladium on barium sulfate, palladium on aluminum silicates such as montmorillonite, palladium on $SiO_2$ and palladium on calcium carbonate, in each case having a palladium content of from 0.5 to 10% by weight, particularly preferably palladium in powdered form and also palladium on activated carbon, palladium on barium and calcium carbonate, and palladium on barium sulfate, in each case having a palladium content of from 0.5 to 10% by weight, in particular palladium on activated carbon having a palladium content of 10% by weight.

It is also possible to use catalysts which contain further dopants, e.g. lead (Lindlar catalyst), in addition to palladium and the supporting material.

The metallic palladium catalyst is used in the process of the invention in a proportion of from 0.1 to 10 mol %, preferably from 0.2 to 5 mol %, particularly preferably from 0.5 to 3 mol %, most particularly preferably from 0.5 to 1.5 mol %, based on the aromatic halogen compound or the perfluoroalkylsulfonate.

Suitable ligands for the process of the invention are, for example, phosphines such as trialkylphosphines, tricycloalkylphosphines, triarylphosphines, where the three substituents on the phosphorus can be identical or different, chiral or achiral and where one or more of the ligands can link the phosphorus groups of a plurality of phosphines and where a part of this linkage can also be one or more metal atoms.

Examples of phosphines which can be used for the purposes of the process of the invention are trimethylphosphine, tributylphosphine, tricyclohexylphosphine, triphenylphosphine, tritolylphosphine, tris(4-dimethylaminophenyl)phosphine, bis(diphenylphosphino)methane, 1,2-bis(diphenylphosphino)ethane, 1,3-bis(diphenylphosphino)propane and 1,1'-bis(diphenylphosphino)ferrocene. Further suitable ligands are, for example, diketones, e.g. acetylacetone and octafluoroacetylacetone and tertiary amines, e.g. trimethylamine, triethylamine, tri-n-propylamine and triisopropylamine.

Preferred ligands are phosphines and diketones, particular preference being given to phosphines. Very particularly preferred ligands are triphenylphosphine, 1,2-bis(diphenylphosphino)ethane, 1,3-bis(diphenylphosphino)propane and 1,1'-bis(diphenylphosphino)ferrocene, in particular triphenylphosphine. The ligand is used in the process of the invention in a proportion of from 0.1 to 20 mol %, preferably from 0.2 to 15 mol %, particularly preferably from 0.5 to 10 mol %, most particularly preferably from 1 to 6 mol %, based on the aromatic halogen compound or the perfluoroalkylsulfonate.

It is also possible, if desired, to use mixtures of two or more different ligands.

One class of starting compounds for the process of the invention consists of aromatic boronic acids, preferably those of the formula II, $$R^1(-A^1)_k(-M^1)_l-A^2-B(OH)_2 \qquad (II)$$

where $R^1$, $A^1$, $A^2$, $M^1$, k and l are as defined below:

$R^1$ is benzyloxy, H, F, Cl, Br, —NC, —CN, —$CF_3$, —$OCF_3$ or a straight-chain or branched alkyl radical (with or without an asymmetric carbon atom) having from 1 to 18 carbon atoms, where one or two nonadjacent —$CH_2$— groups can also be replaced by —O—, —S—, —CO—, —CO—O—, —O—CO—, —CO—S—, —S—CO—, —O—CO—O—, —CH=CH—, —C≡C—, 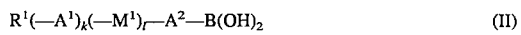 or —Si($CH_3$)$_2$—, and where one or more hydrogen atoms of the alkyl radical can also be replaced by F, Cl, Br or CN, $A^1$ is 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, trans-1,4-cyclohexylene, where one or two nonadjacent $CH_2$ groups can be replaced by —O— or —S— and where one or two hydrogen atoms can be replaced by halogen atoms, cyano and/or methyl groups, (1,3,4)-thiadiazole-2,5-diyl, 1,3-thiazol-2,4-diyl, 1,3-thiazol-2,5-diyl, thiophene-2,4-diyl, thiophene-2,5-diyl, piperazine-1,4-diyl, piperazine-2,5-diyl, piperidine-1,4-diyl, naphthalene-2,6-diyl, bicyclo[2.2.2]octane-1,4-diyl, 1,3-dioxaborinane-2,5-diyl or trans-decalin-2,6-diyl, $A^2$ is 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, 1,3,4-thiadiazole-2,5-diyl, 1,3-thiazol-2,4-diyl, 1,3-thiazol-2,5-diyl, thiophene-2,4-diyl, thiophene-2,5-diyl or naphthalene-2,6-diyl, $M^1$ is —O—, —S—, —CO—, —CO—O—, —O—CO—, —CO—S—, —S—CO—, —O—CO—O—, —$CH_2$—O—, —O$CH_2$—, —$CH_2CH_2$—, —CH=CH—, —C≡C—, —CH(CN)—$CH_2$—, —$CH_2$—CH(CN)—, —CH=N—, —N=CH—, —$CH_2CH_2CH_2$—O—, —O$CH_2$CH$_2$CH$_2$—, —$CH_2CH_2$CO—O—, —O—COCH$_2$CH$_2$— and k, l are each, independently of one another, zero or one.

Preferably, $R^1$ is benzyloxy, H, F, Cl, —$CF_3$, $OCF_3$ or a straight-chain or branched alkyl radical (with or without an asymmetric carbon atom) having from 1 to 18 carbon atoms, where one or two nonadjacent —$CH_2$— groups can also be replaced by —O—, —CO—, —CO—O—, —OCO—, —O—CO—O—, —CH=CH—, —C≡C—, 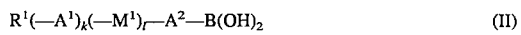 or —Si($CH_3$)$_2$—, and where one or more hydrogen atoms of the alkyl radical can also be replaced by F, Cl or CN.

Particularly preferably, $R^1$ is benzyloxy, H or a straight-chain or branched alkyl radical (with or without an asymmetric carbon atom) having from 1 to 18 carbon atoms, where one or two nonadjacent —CH$_2$— groups can also be replaced by —O—, —CH=CH—, —C≡C—, △ or —Si(CH$_3$)$_2$—.

Preferably, $A^1$ is 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, trans-1,4-cyclohexylene where one or two nonadjacent —CH$_2$— groups can be replaced by —O—, (1,3,4)-thiadiazol-2,5-diyl, naphthalene-2,6-diyl or bicyclo[2.2.2]octane-1,4-diyl.

Particularly preferably, $A^1$ is 1,4-phenylene, 2-fluoro-1,4-phenylene, 2,3-difluoro-1,4-phenylene, 2,6-difluoro-1,4-phenylene, 2,5-difluoro-1,4-phenylene, and also pyridine-2,5-diyl, pyrimidine-2,5-diyl, where one or two hydrogen atoms can be replaced by fluorine, or trans-1,4-cyclohexylene.

Preferably, $A^2$ is 1,4-phenylene, pyrazine-2,5-diyl, pyridazine-3,5-diyl, pyridine-2,5-diyl, pyrimidine-2,5-diyl, where one or two hydrogen atoms can be replaced by halogen atoms, or naphthalene-2,6-diyl.

Particularly preferably, $A^2$ is 1,4-phenylene, 2-fluoro-1,4-phenylene, 2,3-difluoro-1,4-phenylene, 2,6-difluoro-1,4-phenylene, 2,5-difluoro-1,4-phenylene, and also pyridine-2,5-diyl where one or two hydrogen atoms can be replaced by F, or naphthalene-2,6-diyl.

Preferably, $M^1$ is —O—, —CO—, —CO—O—, —O—CO—, —O—CO—O—, —CH$_2$—O—, —O—CH$_2$—, —CH$_2$—CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$CH$_2$—.

Particularly preferably, $M^1$ is —O—, —CH$_2$—O—, —O—CH$_2$—, —CH$_2$—CH$_2$—, —CH=CH— or —C≡C—.

Most particularly preferred are the aromatic boronic acids of the formulae IIa to IIh listed below:

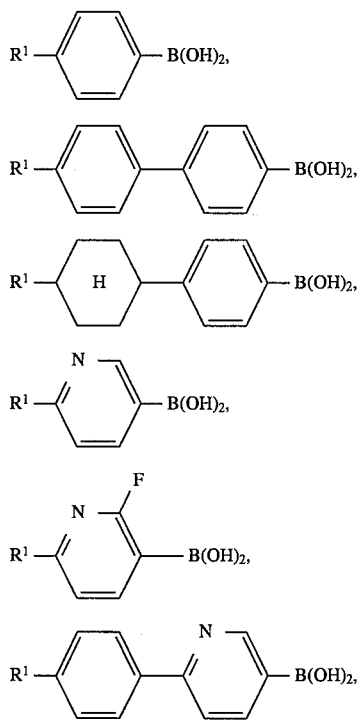

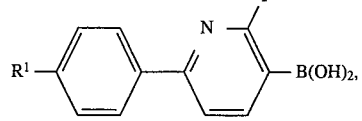

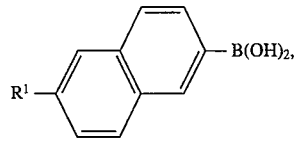

where $R^1$ is benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy and pentadecoxy.

The aromatic boronic acids used, preferably those of the formula II, are either known or can be prepared by known methods, as described, for example, in Houben Weyl Methoden der Organischen Chemie, Georg Thieme-Verlag, Stuttgart, Volume 13/3a. Thus it is possible, for example, to obtain boronic acids, preferably those of the formula II, from aromatic alkali metal and magnesium compounds by reaction with trialkoxyboranes and subsequent hydrolysis.

The second class of starting compounds for the process of the invention consists of aromatic halogen compounds or aromatic perfluoroalkylsulfonates, preferably those of the formula III, $$X—A^3(—M^2)_m(—A^4)_n—R^2 \quad (III)$$

where $R^2$, $A^3$, $A^4$, $M^2$, $X$, m and n are as defined below.

$R^2$ ie benzyloxy, H, F, Cl, Br, —NC, —CN, —CF$_3$, —OCF$_3$ or a straight-chain or branched alkyl radical (with or without an asymmetric carbon atom) having from 1 to 18 carbon atoms, where one or two nonadjacent —CH$_2$— groups can also be replaced by —O—, —S—, —CO—, —CO—O—, —O—CO—, —CO—S—, —S—CO—, —O—CO—O—, —CH=CH—, —C≡C—, △ or —Si(CH$_3$)$_2$—, and where one or more hydrogen atoms of the alkyl radical can also be replaced by F, Cl, Br or CN, $A^4$ is 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, trans-1,4-cyclohexylene, where one or two nonadjacent CH$_2$ groups can be replaced by —O— or —S— and where one or two hydrogen atoms can be replaced by halogen atoms, cyano and/or methyl groups, (1,3,4)-thiadiazole-2,5-diyl, 1,3-thiazol-2,4-diyl, 1,3-thiazol-2,5-diyl, thiophene-2,4-diyl, thiophene-2,5-diyl, piperazine-1,4-diyl, piperazine-2,5-diyl, piperidine-1,4-diyl, naphthalene-2,6-diyl, bicyclo[2.2.2]octane-1,4-diyl, 1,3-dioxaborinane-2,5-diyl or trans-decalin-2,6-diyl, $A^3$ is 1,4-phenylene, pyrazine-2,5-diyl, pyridazine-3,6-diyl, pyridine-2,5-diyl, pyrimidine-2,5-diyl, where one or two hydrogen atoms can also be replaced by halogen atoms, cyano and/or methyl groups, 1,3,4-thiadiazole-2,5-diyl, 1,3-thiazol-2,4-diyl, 1,3-thiazol-2,5-diyl, thiophene-2,4-diyl, thiophene-2,5-diyl or naphthalene-2,6-diyl, $M^2$ is —O—, —S—, —CO—, —CO—O—, —O—CO—, —CO—S—, —S—CO—, —O—CO—O—, —CH$_2$—O—, —OCH$_2$—, —CH$_2$CH$_2$—, —CH=CH—, —C≡C—, —CH(CN)—CH$_2$—, —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$— and m, n are each, independently of one another, zero or one.

Preferably, $R^2$ is benzyloxy, H, F, Cl, Br, —CN, —CF$_3$, OCF$_3$ or a straight-chain or branched alkyl radical (with or without an asymmetric carbon atom) having from 1 to 18 carbon atoms, where one or two nonadjacent —CH$_2$— groups can also be replaced by —O—, —CO—, —CO—O—, —O—CO—, —O—CO—O—, —CH=CH—, —C≡C—, △ or —Si(CH$_3$)$_2$—, and where one or more hydrogen atoms of the alkyl radical can also be replaced by F, Cl or CN.

Particularly preferably, $R^2$ is benzyloxy, H, Cl, Br or a straight-chain or branched alkyl radical (with or without an asymmetric carbon atom) having from 1 to 18 carbon atoms, where one or two nonadjacent —CH$_2$— groups can also be replaced by —O—, —CO—, —CO—O—, —O—, —O—CO—, —O—CO—O—, —CH=CH—, —C≡C—, △ or —Si(CH$_3$)—.

Preferably, $A^3$ is 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, 1,3,4-thiadiazol-2,5-diyl or naphthalene-2,6-diyl.

Particularly preferably, $A^3$ is 1,4-phenylene, 2-fluoro-1,4-phenylene, 2,3-difluoro-1,4-phenylene, 2,6-difluoro-1,4-phenylene, 2,5-difluoro-1,4-phenylene, and also pyrazine-2,5-diyl, pyridazine-2,5-diyl, pyrimidine-2,5-diyl, where one or two hydrogen atoms can be replaced by halogen atoms or naphthalene-2,6-diyl.

Preferably, $A^4$ is 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, trans-1,4-cyclohexylene, where one or two nonadjacent CH$_2$ groups can be replaced by —O—, (1,3,4)-thiadiazole-2,5-diyl, naphthalene-2,6-diyl or bicyclo[2.2.2]octane-1,4-diyl.

Particularly preferably, $A^4$ is 1,4-phenylene, 2-fluoro-1,4-phenylene, 2,3-difluoro-1,4-phenylene, 2,6-difluoro-1,4-phenylene, 2,5-difluoro-1,4-phenylene, and also pyridine-2,5-diyl, pyrimidine-2,5-diyl, where one or two hydrogen atoms can be replaced by F, or trans-1,4-cyclohexylene.

Preferably, $M^2$ is —O—, —CO—, —CO—O—, —O—CO—, —O—CO—O—, —CH$_2$—O—, —O—CH$_2$—, —CH$_2$—CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$CH$_2$—.

Particularly preferably, $M^2$ is —O—, —CO—, —CO—O—, —O—CO—, —O—CO—O—, —CH$_2$—O—, —O—CH$_2$—, —CH$_2$—CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$CH$_2$—.

Preferably, X is chlorine, bromine or OSO$_2$—C$_p$F$_{2p+1}$, where p is an integer from 1 to 10. Particularly preferably, X is chlorine or bromine.

Most particularly preferred are the aromatic halogen compounds of the formula III 1 to III 24 shown below,

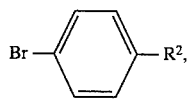

III 1

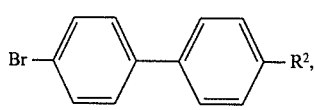

III 2

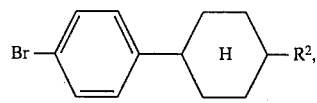

III 3

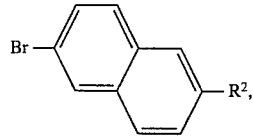

III 4

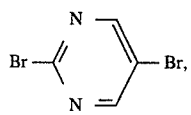

III 5

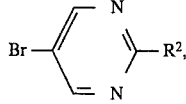

III 6

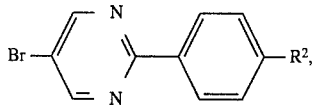

III 7

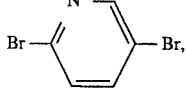

III 8

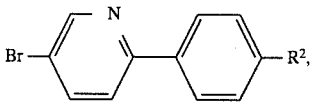

III 9

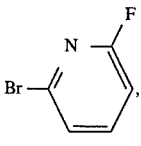

III 10

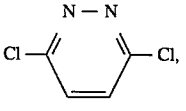

III 11

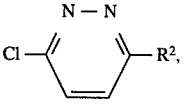

III 12

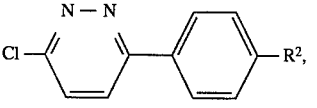

III 13

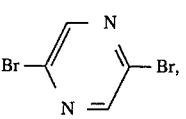

III 14

III 15

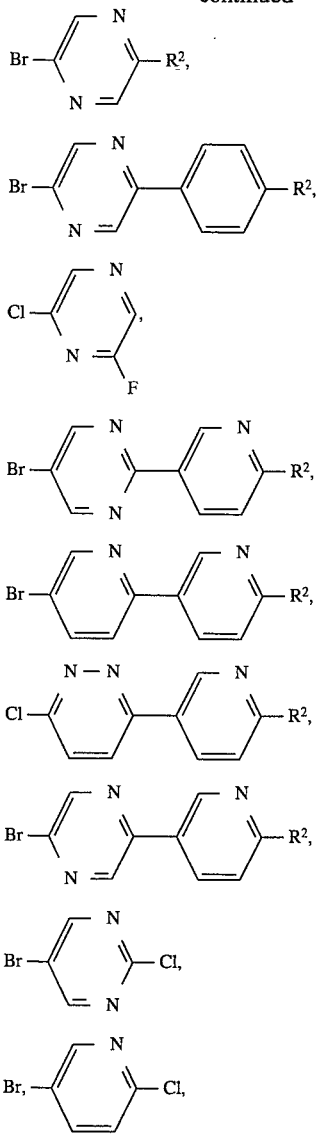

where $R^2$ is benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy and pentadecoxy.

The aromatic halogen compounds and perfluoroalkylsulfonates preferably those of the general formula III, are either known or can be prepared by known methods, as are described, for example, in Houben Weyl, Methoden der Organischen Chemie, Georg Thieme-Verlag, Stuttgart, Volume 5/3 and 5/4. For example, the aromatic halides can be obtained by replacing the diazonium group in a corresponding diazonium salt by chlorine, bromine or iodine.

Furthermore, hydroxy-substituted nitrogen heterocycles can be converted by means of phosphorus trihalides and phosphorus oxytrihalides into the corresponding halides. The process of the invention for cross-coupling aromatic boronic acids with aromatic halogen compounds or perfluoroalkylsulfonates can likewise be used for preparing compounds of the formula III. Perfluoroalkylsulfonates of the formula III, where X is $OSO_2$—$C_nH_{2n+1}$, can be prepared by esterification of corresponding alcohols of the formula III, where X is a hydroxyl group, with perfluoroalkanesulfonic acids or their reactive derivatives. The corresponding perfluoroalkanesulfonic acids are known. Suitable reactive derivatives of the said perfluoroalkanesulfonic acids are, in particular, the acid halides, especially the chlorides and bromides, also the anhydrides.

Products of the process of the invention are polycyclic aromatic compounds.

Preferred products of the process of the invention are compounds of the formula I, $$R^1(-A^1)_k(-M^1)_l-A^2-A^3(-M^2)_m(-A^4)_n-R^2 \quad (I)$$

where $R^1$ and $R^2$ can be, independently of one another, benzyloxy, H, F, Cl, Br, —NC, —CN, —$CF_3$, —$OCF_3$ or a straight-chain or branched alkyl radical (with or without an asymmetric carbon atom) having from 1 to 18 carbon atoms, where one or two nonadjacent —$CH_2$ groups can also replaced by —O—, —S—, —CO—, —CO—O—, —O—CO—, —CO—S—, —S—CO—, —O—CO—O—, —CH═CH—, —C≡C—, △ or —Si(CH$_3$)$_2$—, and where one or more hydrogen atoms of the alkyl radical can also be replaced by F, Cl, Br or CN, $A^1$ and $A^4$ can each be, independently of one another, 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, trans-1,4-cyclohexylene where one or two nonadjacent $CH_2$ groups can be replaced by —O— or —S— and where one or two hydrogen atoms can be replaced by halogen atoms, cyano and/or methyl groups, (1,3,4)-thiadiazole-2,5-diyl, 1,3-thiadiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, naphthalene-2,6-diyl, bicyclo[2.2.2]octane-1,4-diyl, 1,3-dioxaborinane-2,5-diyl or trans-decalin-2,6-diyl, $A^2$ and $A^3$ can each be, independently of one another, 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, 1,3,4-thiadiazole-2,5-diyl, 1,3-thiazole-2,4-diyl, 1,3-thiazole-2,5-diyl, thiophene-2,4-diyl, thiophene-2,5-diyl or naphthalene-2,6-diyl, $M^1$ and $M^2$ can each be, independently of one another, —O—, —S—, —CO—, —CO—O—, —O—CO—, —CO—S, —S—CO—, —O—CO—O—, —$CH_2$—O—, —$OCH_2$—, —$CH_2CH_2$—, —CH═CH—, —C≡C—, —CH(CN)—$CH_2$—, —$CH_2$—CH(CN)—, —CH═N—, —N═CH—, —$CH_2CH_2CH_2$—O—, —$OCH_2CH_2CH_2$—, —$CH_2CH_2CO$—O—, —O—$COCH_2CH_2$—, and k, l, m, n are each, independently of one another, zero or one.

Preferred and particularly preferred variants of $R^1$, $R^2$, $A^1$, $A^2$, $A^3$, $A^4$, $M^1$, $M^2$, k, l, m, n are specified in the formulae II and III.

Most particularly preferred are the compounds of the formula I 1 to I 94 shown below

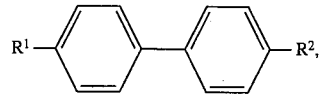

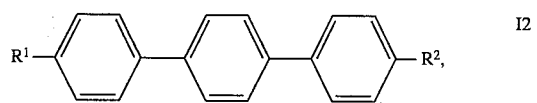

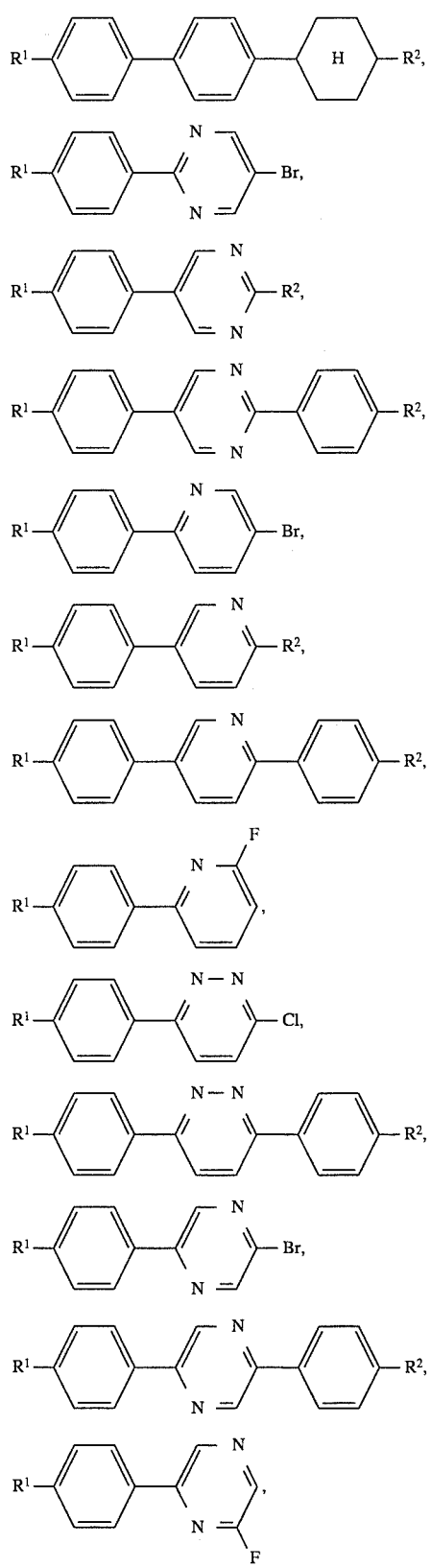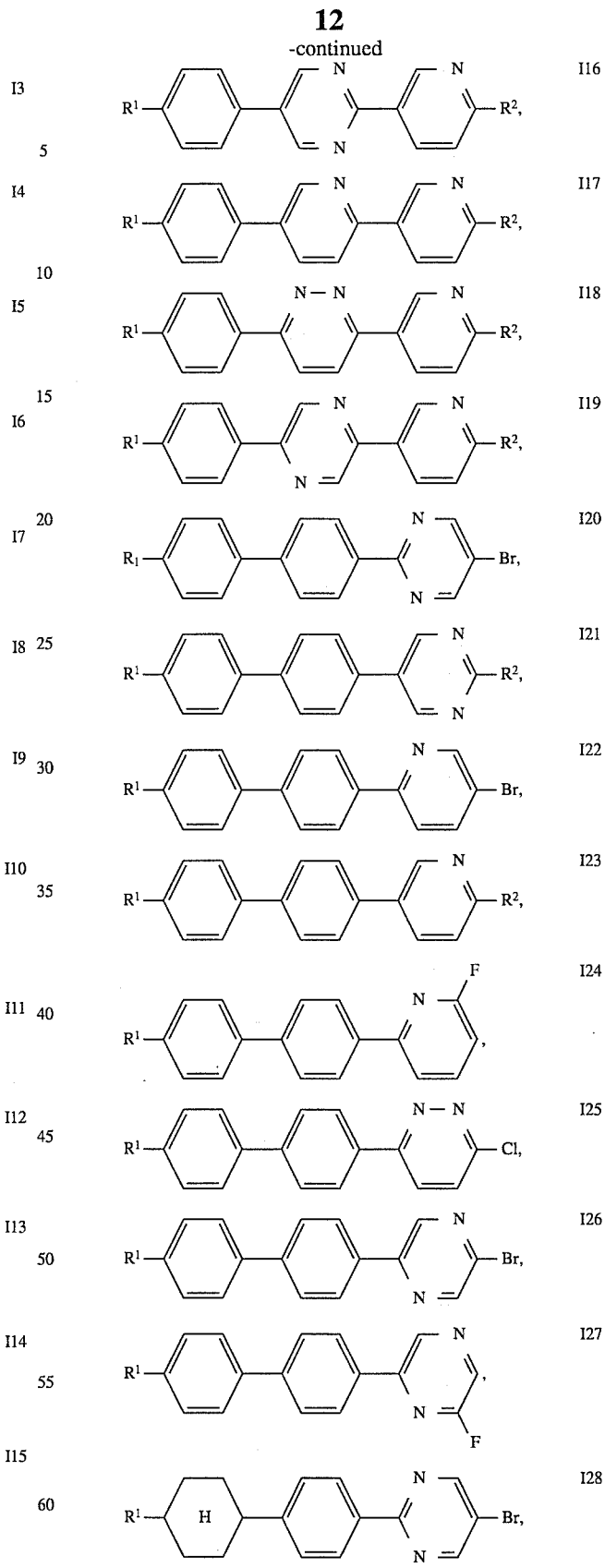

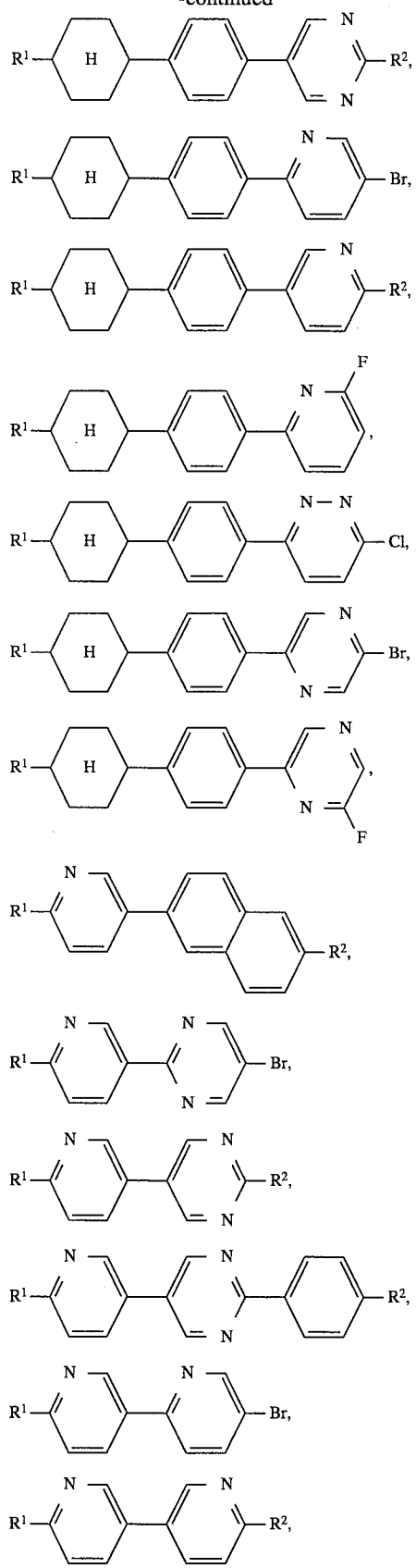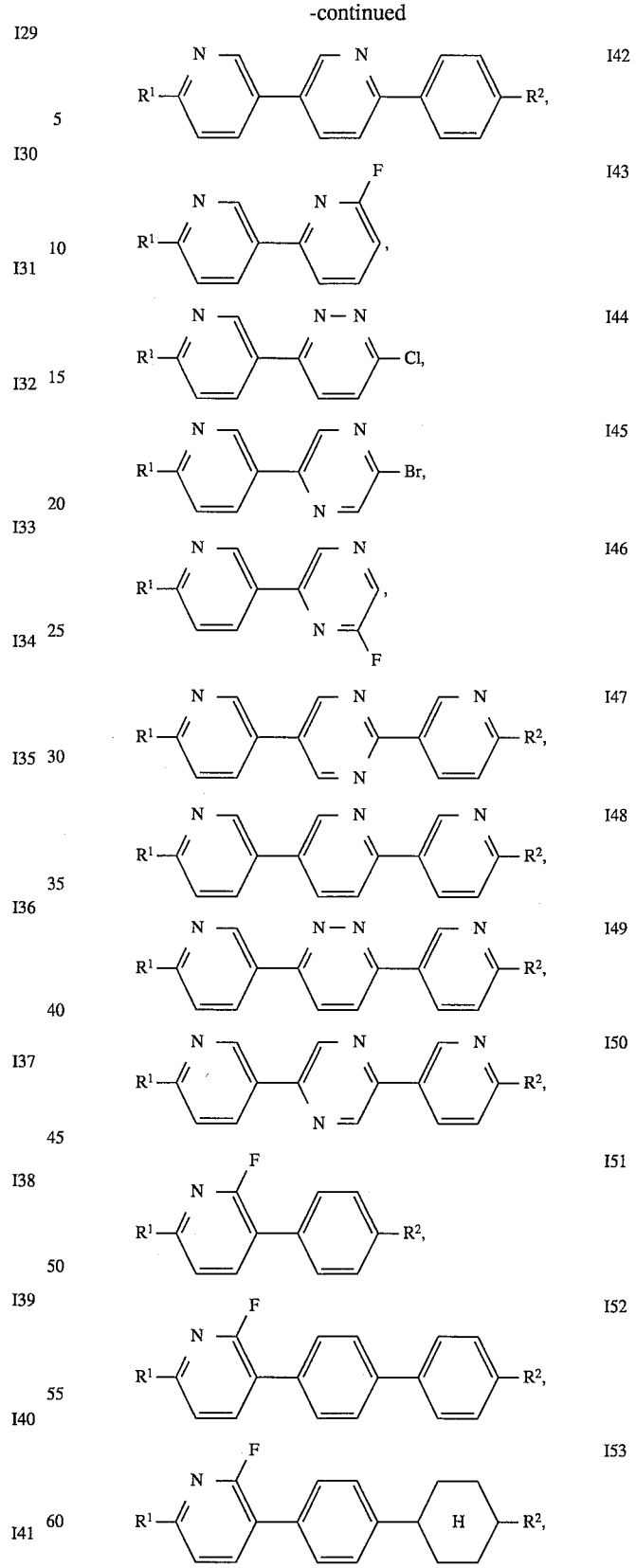

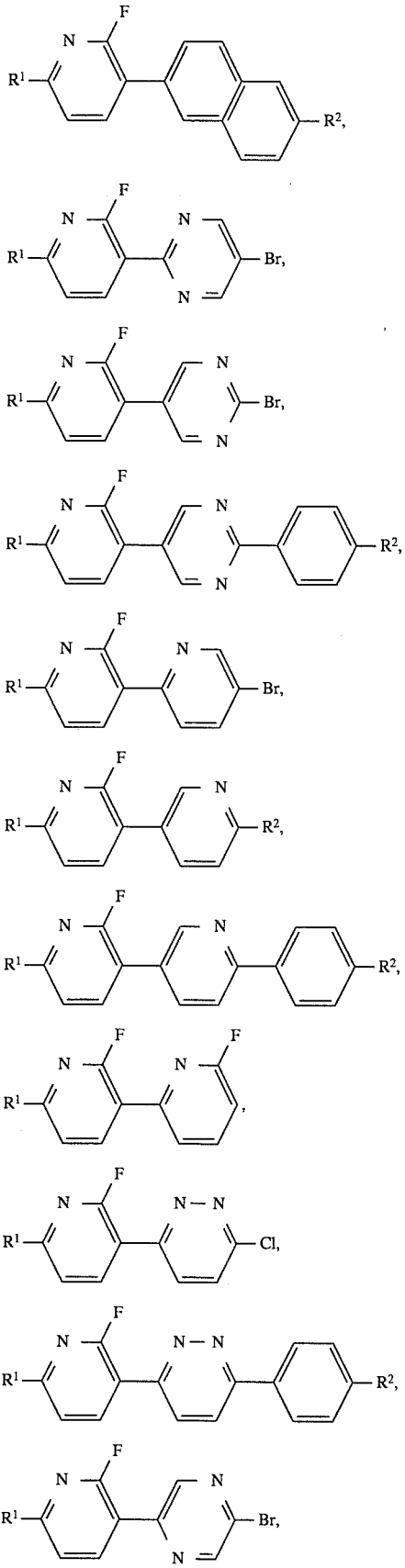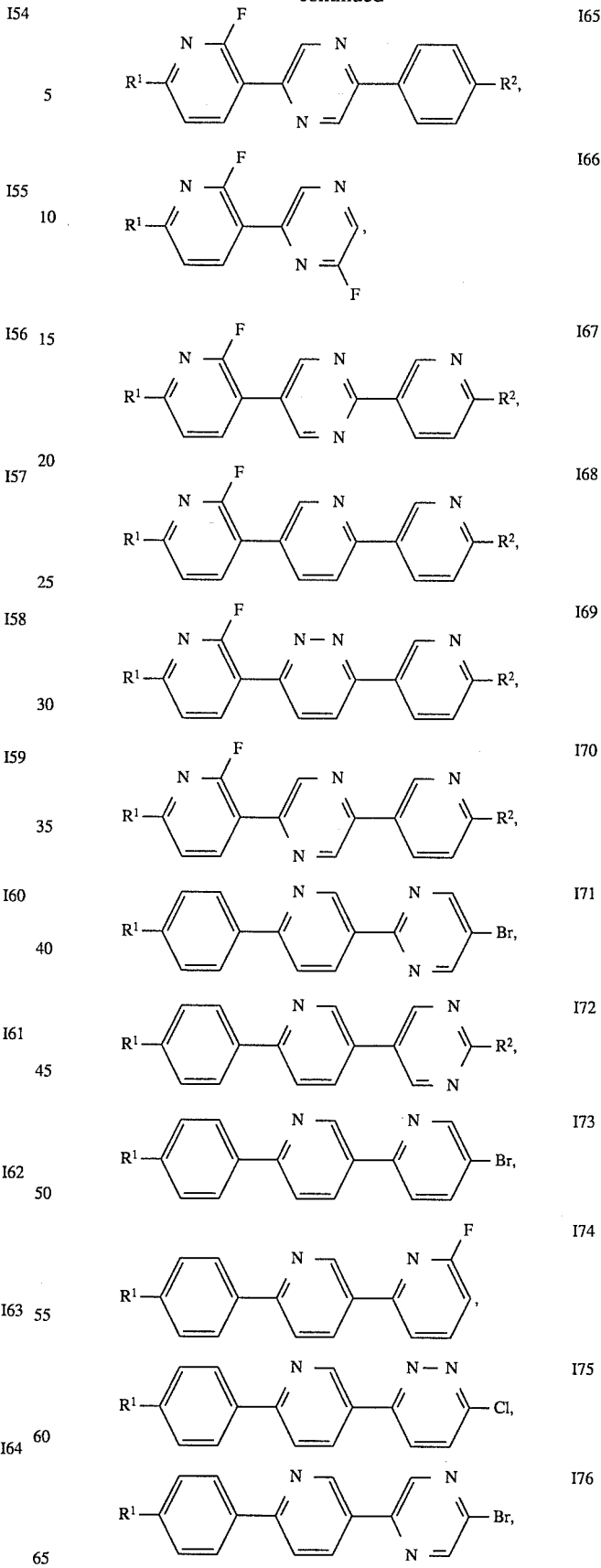

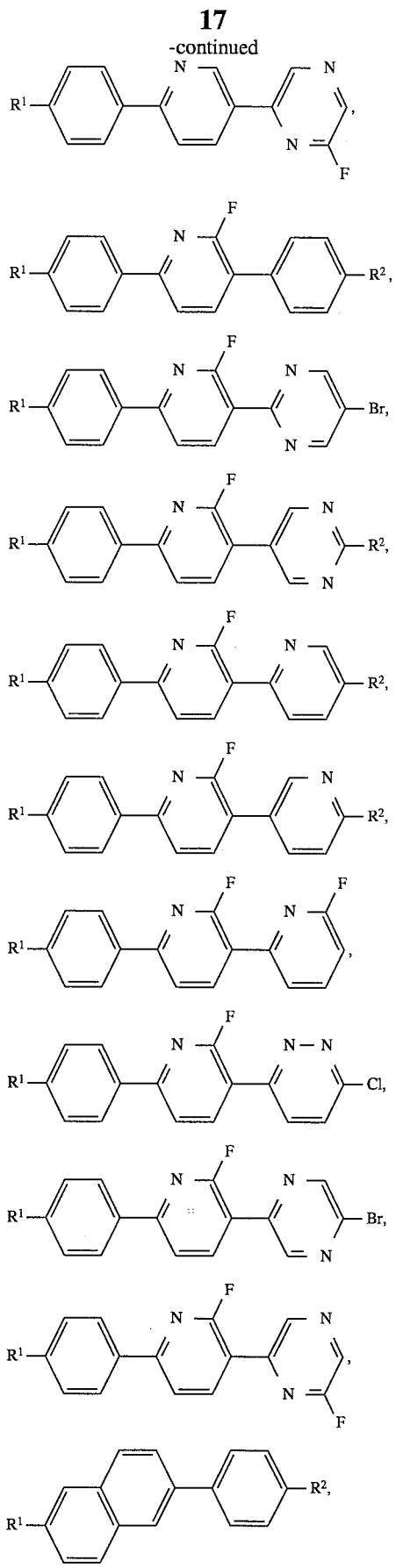
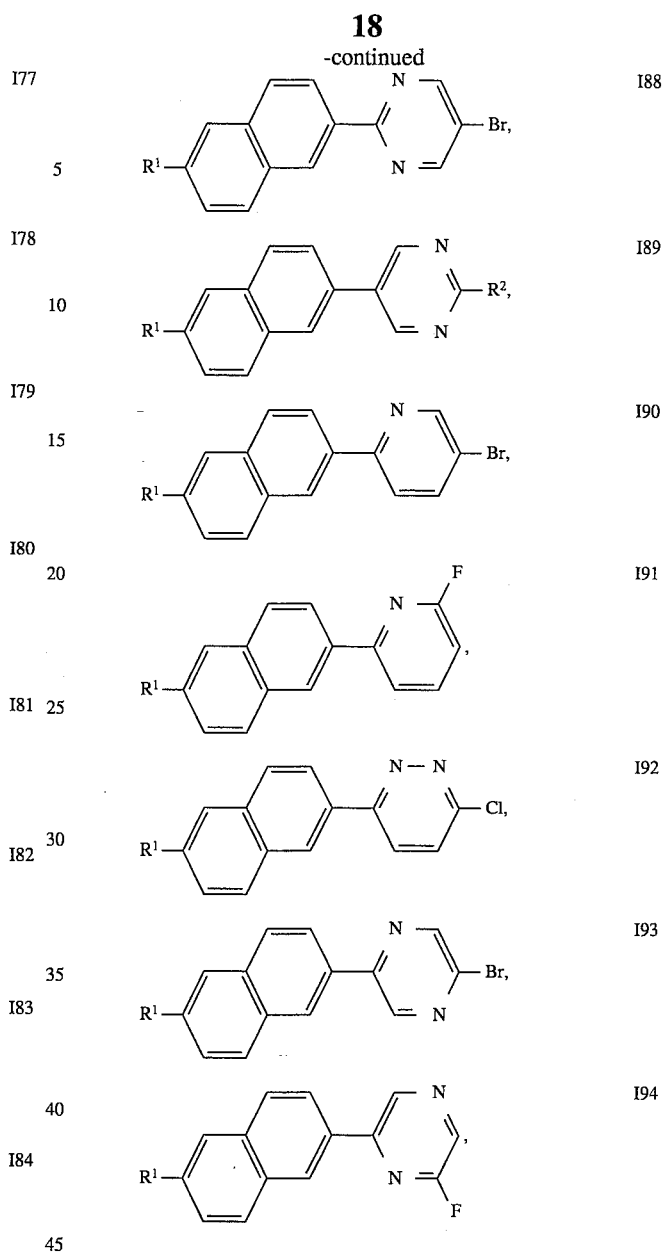

where $R^1$ and $R^2$ are benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy and pentadecoxy.

The compounds of the formula I are suitable for use as liquid-crystalline materials, or can be used as intermediates for the preparation of further liquid-crystalline compounds. Furthermore, compounds of the formula I are also suitable as precursors for pharmaceuticals, cosmetics, fungicides, herbicides, insecticides, dyes, detergents and polymers, including additives for the same.

The present invention is illustrated by the Examples described below, without however being limited, where the abbreviations used have the following meanings:
mp.=melting point
X=crystalline
S=smectic
$S_C$=smectic C
$S_A$=smectic A N=nematic
I=isotropic

EXAMPLE 1

5-Bromo-2-[4-(phenylmethoxy)phenyl]pyrimidine 104.25 g (0.438 mol) of 2,5-dibromopyrimidine, 100.00 g (0.438 mol) of 4-(phenylmethoxy)benzeneboronic acid, 4.75 g (0.00438 mol) of palladium (10%) on activated carbon, 4.50 g (0.01752 mol) of triphenylphosphine and 93.00 g (0.876 mol) of sodium carbonate are heated in 1000 ml of toluene, 500 ml of ethanol and 300 ml of water for 24 hours at 80° C. The palladium catalyst is subsequently separated off from the reaction mixture at 80° C. by filtration. The aqueous lower phase of the reaction mixture is separated off at 80° C., before the organic phase is freed of the solvents on a rotary evaporator and dried in a high vacuum. The crude product thus obtained is recrystallized from acetonitrile (3000 ml), giving 150.07 g (97% yield, based on 2,5-dibromopyridine) of 5-bromo-2-[4-(phenylmethoxy)phenyl]pyrimidine (purity according to HPLC: 98%).

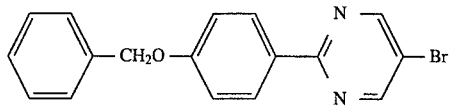

mp.: 153°–155° C.

COMPARATIVE EXAMPLE 1

Synthesis of
5-bromo-2-[4-(phenylmethoxy)phenyl]pyrimidine
by the process described in DE 39 30 663

4.17 g (17.54 mmol) of 2,5-dibromopyrimidine, 4.00 g (17.54 mmol) of 4-(phenylmethoxy)benzeneboronic acid, 0.19 g (0,175 mmol) of palladium (10%) on activated carbon and 3.72 g (35.10 mmol) of sodium carbonate are reacted in 42 ml of toluene, 21 ml of ethanol and 12.5 ml of water using a similar method to Example 1.

Analysis (HPLC) of the crude product indicates a mixture which contains the starting materials 2,5-dibromopyrimidine, 4-(phenylmethoxy)benzeneboronic acid and unidentified products in addition to 6.3% of the desired product 5-bromo-2-[4-(phenylmethoxy)phenyl]pyrimidine.

| Example No. | R¹ | A¹ | A² | A³ | A⁴ | R² | Yield | Phase transitions |
|---|---|---|---|---|---|---|---|---|
| 2 | $H_{17}C_8O$ | |  | 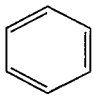 | | Br | 97% | |
| 3 | 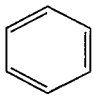 | | 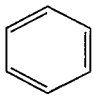 | 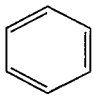 | | Br | 99% | |
| 4 | $H_{17}C_8O$ | | 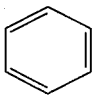 | 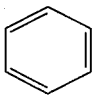 | | Br | 96% | |
| 5 | H | | 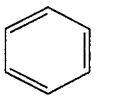 | 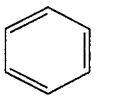 | | Br | 93% | |
| 6 | $H_{13}C_6$ | | 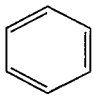 | 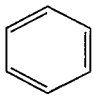 | 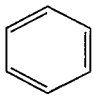 | H | 98 | X 97 $S_A$ 133 I |
| 7 | $H_{13}C_6O$ | | 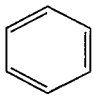 | 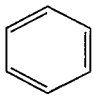 | 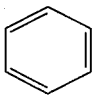 | H | 95% | X 92 $S_A$ 163 I |
| 8 | $H_{13}C_6$ | | 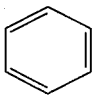 | 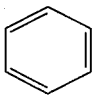 | 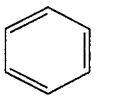 | $O(CH_2)_4CH=CH_2$ | 90% | X 70 $S_4$ 62 $S_3$ 108 $S_C$ 146 $S_A$ 189 I |
| 9 | 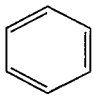 | | 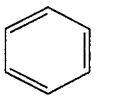 | 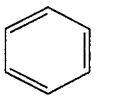 | | H | 85% | |

-continued

| Example No. | R¹ | A¹ | A² | A³ | A⁴ | R² | Yield | Phase transitions |
|---|---|---|---|---|---|---|---|---|
| 10 | $H_{17}C_8O$ | | phenyl | 2-fluoropyridyl | H | | 91% | |
| 11 | $H_{17}C_8O$ | | difluorophenyl | 2-fluoropyridyl | H | | 87% | |
| 12 | $H_{17}C_8O$ | | phenyl | pyrimidinyl | H | | 81% | |
| 13 | H | | phenyl | pyrimidinyl | pyridyl | $O(CH_2)_8CH{=}CH_2$ | 92% | X 96 $S_A$ 91 |
| 14 | cyclopropyl-$(CH_2)_3O$ | | phenyl | pyrimidinyl | Br | | 95% | |
| 15 | $H_{17}C_8O$ | phenyl | phenyl | 2-fluoropyridyl | H | | 83% | X 148 $S_3$ 149 $S_C$ 150 $S_A$ 162 I |
| 16 | $H_{17}C_8O$ | phenyl | phenyl | 2-fluoropyridyl | H | | 80% | X 95 $S_3$ 111 $S_C$ 116 $S_A$ 132 I |

-continued

| Example No. | R¹ | A¹ | A² | A³ | A⁴ | R² | Yield | Phase transitions |
|---|---|---|---|---|---|---|---|---|
| 17 | $H_7C_3$ | cyclohexyl-H | phenyl | pyrimidine | | Br | 93% | |
| 18 | $H_{11}C_5$ | cyclohexyl-H | phenyl | pyrimidine | | Br | 89% | |
| 19 | $H_{17}C_8$ | cyclohexyl-H | phenyl | pyrimidine | | Br | 90% | |
| 20 | $H_{11}C_5$ | cyclohexyl-H | phenyl | F-pyridine | | H | 85% | |
| 21 | $H_{11}C_5$ | cyclohexyl-H | phenyl | F-pyrimidine | | H | 82% | |
| 22 | $H_{17}C_8O$ | | pyridine | pyrimidine | | Br | 89% | |
| 23 | $H_2C=CH(CH_2)_8O$ | | pyridine | pyrimidine | | Br | 93% | |
| 24 | $H_{17}C_8O$ | | pyridine | pyrimidine | | $OC_8H_{17}$ | 96% | X 64 $S_C$ 67 $S_A$ 91 I |

-continued

| Example No. | R¹ | A¹ | A² | A³ | A⁴ | R² | Yield | Phase transitions |
|---|---|---|---|---|---|---|---|---|
| 25 | $H_{17}C_8O$ | | pyridine | pyrazine | | $O(CH_2)_8CH=CH_2$ | 80% | X 59 $S_C$ 66 $S_A$ 80 I |
| 26 | $H_{13}C_6O$ | | pyridine | pyrazine | | $O(CH_2)_8CH=CH_2$ | 83% | X 56 $S_A$ 80 I |
| 27 | $H_{21}C_{10}O$ | | pyridine | pyrazine | | $OC_8H_{17}$ | 90% | X 67 $S_C$ 74 $S_A$ 89 I |
| 28 | $H_2C=CH(CH_2)_8O$ | | pyridine | pyrazine | | $C_8H_{17}$ | 94% | X (65) $S_A$ 64 I |
| 29 | $H_2C=CH(CH_2)_8O$ | | pyridine | pyrazine | benzene | H | 96% | X 87 $S_A$ 125 I |
| 30 | H | | benzene | pyridine | | Br | 82% | |
| 31 | H | benzene | pyridine | pyrazine | | $OC_{10}H_{21}$ | 90% | X 125 $S_A$ 154 I |
| 32 | H | benzene | pyridine | pyrazine | | $OC_8H_{17}$ | 92% | X 133 $S_A$ 153 I |
| 33 | H | benzene | pyridine | pyrimidine | | Br | 87% | |

-continued

| Example No. | R¹ | A¹ | A² | A³ | A⁴ | R² | Yield | Phase transitions |
|---|---|---|---|---|---|---|---|---|
| 34 | H₁₇C₈O | | pyridine (N) | pyrazine (N,N) | benzene | OC₂H₅ | 93% | X 91 S_C 100 S_A 218 I |
| 35 | H₁₇C₈O | | pyridine (N) | pyrazine (N,N) | benzene | OC₈H₁₇ | 96% | X 91 S_C 190 S_A 194 I |
| 36 | H₁₇C₈O | | pyridine (N) | pyrazine (N,N) | benzene | O(CH₂)₉CH=CH₂ | 87% | X 83 S_C 175 S_A 179 I |
| 37 | H₁₇C₈O | | pyridine (N) | pyrazine (N,N) | benzene | O(CH₂)₂CH=CH₂ | 90% | X 89 S_C 159 S_A 207 I |
| 38 | H₁₇C₈O | | F-pyridine | benzene | | OC₈H₁₇ | 85% | |
| 39 | H₁₇C₈O | | F-pyridine | benzene | benzene | OC₈H₁₇ | 92% | X 87 S₃ 116 S_C 158 S_A 163 I |
| 40 | H₁₃C₆O | | F-pyridine | benzene | benzene | OC₈H₁₇ | 96% | X 85 S₄ 93 S₃ 119 S_C 161 S_A 169 I |

-continued

| Example No. | R¹ | A² | A³ | A⁴ | R² | Yield | Phase transitions |
|---|---|---|---|---|---|---|---|
| 41 | H₁₇C₈O | 2-F-pyridine | phenyl | phenyl | C₈H₁₇ | 99% | X 62 S₃ 96 S_C 116 S_A 133 I |
| 42 | H₁₃C₆O | 2-F-pyridine | phenyl | phenyl | C₈H₁₇ | 96% | X 44 S₄ 92 S₃ 99 S_C 118 S_A 138 I |
| 43 | H₁₇C₈O | 2-F-pyridine | phenyl | 2-F-pyridine | OC₈H₁₇ | 82% | X 91 S_A 95 I |
| 44 | H₁₇C₈O | 2-F-pyridine | pyrimidine | 2-F-pyridine | OC₈H₁₇ | 85% | X 91 S_C 110 S_A 116 I |
| 45 | H₁₇C₈O | 2-F-pyridine | 2,5-difluorophenyl | 2-F-pyridine | OC₈H₁₇ | 81% | X 124 I |
| 46 | H₁₇C₈O | 2-F-pyridine | pyridine | 2-F-pyridine | OC₈H₁₇ | 80% | X 65 S_C 85 S_A 104 I |
| 47 | H₁₇C₈O | 2-F-pyridine | pyridazine | 2-F-pyridine | OC₈H₁₇ | 87% | X 100 S_C 127 N 128 I |

-continued

| Example No. | R¹ | A¹ | A² | A³ | A⁴ | R² | Yield | Phase transitions |
|---|---|---|---|---|---|---|---|---|
| 48 | H₁₇C₈O | | 2-F pyridine | phenyl | cyclohexyl | C₅H₁₁ | 93% | X 78 S_A 110 N 117 I |
| 49 | H₂₁C₁₀O | | 2-F pyridine | phenyl | cyclohexyl | C₅H₁₁ | 89% | X 64 S_A 108 N 112 I |
| 50 | H₂₅C₁₂O | | 2-F pyridine | phenyl | cyclohexyl | C₅H₁₁ | 90% | X 62 S_A 104 N 107 I |
| 51 | H₁₇C₈O | | 2-F pyridine | naphthyl | | OC₈H₁₇ | 94% | X 58 S_A 86 I |
| 52 | H₁₇C₈O | phenyl | 2-F pyridine | phenyl | | OC₆H₁₃ | 86% | X 105 S_C 174 N 188 I |
| 53 | H₁₇C₈O | phenyl | 2-F pyridine | phenyl | | OC₈H₁₇ | 80% | X 105 S_C 176 N 182 I |
| 54 | H₁₇C₈O | phenyl | phenyl | phenyl | | C₇H₁₅ | 81% | X 58 S₂ 65 S_C 157 N 164 I |

-continued

| Example No. | R¹ | A¹ | A² | A³ | A⁴ | R² | Yield | Phase transitions |
|---|---|---|---|---|---|---|---|---|
| 55 | $H_{17}C_8O$ | phenyl | 2-fluoropyridine | phenyl | | $C_6H_{13}$ | 83% | X 55 S₂ 58 S_C 153 N 163 I |
| 56 | $H_{17}C_8O$ | phenyl | 2-fluoropyridine | phenyl | | H | 91% | |
| 57 | H | phenyl | 2-fluoropyridine | phenyl | | $OC_8H_{17}$ | 86% | X 107 (80) S_A 85 N 101 I |
| 58 | $H_{17}C_8O$ | phenyl | 2-fluoropyridine | phenyl | phenyl | $C_8H_{17}$ | 80% | X 73 S₃ 173 S_C 273 S_A 275 N 281 I |
| 59 | $H_{17}C_8O$ | naphthyl | | pyrimidine | | Br | 97% | |
| 60 | $H_{17}C_8O$ | naphthyl | | 2-fluoropyridine | | H | 92% | |

We claim:

1. A process for preparing polycyclic aromatic compounds by cross-coupling aromatic boronic acids with aromatic halogen compounds or perfluoroalkylsulfonates in the presence of metallic palladium, if desired applied to a support material, as catalyst, wherein the coupling is carried out in the presence of a ligand selected from the group consisting of phosphines, diketones and tertiary amines and a base.

2. The process as claimed in claim 1, wherein a polycyclic aromatic compound of the formula I $$R^1(-A^1)_k(-M^1)_l-A^2-A^3(-M^2)_m(-A^4)_n-R^2 \qquad (I)$$

where $R^1$ and $R^2$ can be, independently of one another, benzyloxy, H, F, Cl, Br, —NC, —CN, —CF$_3$, —OCF$_3$ or a straight-chain or branched alkyl radical (with or without an asymmetric carbon atom) having from 1 to 18 carbon atoms, where one or two nonadjacent —CH$_2$ groups can also be replaced by —O—, —S—, —CO—, —CO—O—, —O—CO—, —CO—S—, —S—CO—, —O—CO—O—, —CH=CH—, —C≡C—, 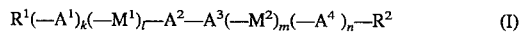 or —Si(CH$_3$)$_2$—, and where one or more hydrogen atoms of the alkyl radical can also be replaced by F, Cl, Br or CN, $A^1$ and $A^4$ can each be, independently of one another, 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, trans-1,4-cyclohexylene where one or two nonadjacent CH$_2$ groups can be replaced by —O— or —S— and where one or two hydrogen atoms can be replaced by halogen atoms, cyano and/or methyl groups, (1,3,4)-thiadiazole-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, naphthalene-2,6-diyl, bicyclo[2.2.2]octane-1,4-diyl, 1,3-dioxaborinane-2,5-diyl or trans-decalin-2,6-diyl, $A^2$ and $A^3$ can each be, independently of one another, 1,4-phenylene, pyrazine-2,5-diyl, pyridazine-3,6-diyl, pyridine-2,5-diyl, pyrimidine-2,5-diyl, where one or two hydrogen atoms can be replaced by halogen atoms, cyano and/or methyl groups, 1,3,4-thiadiazole-2,5-diyl, 1,3-thiazole-2,4-diyl, 1,3-thiazole-2,5-diyl, thiophene-2,4-diyl, thiophene-2,5-diyl or naphthalene-2,6-diyl, $M^1$ and $M^2$ can each be, independently of one another, —O—, —S—, —CO—, —CO—O—, —O—CO—, —CO—S—, —S—CO—, —O—CO—O—, —CH$_2$—O—, —OCH$_2$—, —CH$_2$CH$_2$—, —CH=CH—, —C≡C—, —CH(CN)—CH$_2$— —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$—, k, l, m, n are each, independently of one another, zero or one, is prepared by reacting boronic acids of the formula II $$R^1(-A^1)_k(-M^1)_l-A^2-B(OH)_2 \qquad (II)$$

where $R^1$, $A^1$, $A^2$, $M^1$, k and l are as defined above, with a compound of the formula (III)

$$X-A^3(-M^2)_m(-A^4)_n-R^2 \qquad (III)$$

where $R^2$, $A^3$, $A^4$, $M^2$, m and n are as defined above, and X is chlorine, bromine, iodine or OSO$_2$—C$_p$F$_{2p+1}$, where p is an integer from 1 to 10.

3. The process as claimed in claim 1, wherein the ligand is added in a proportion of 0.1–20 mol %, based on the aromatic halogen compound or the aromatic perfluoroalkylsulfonate.

4. The process as claimed in claim 1, wherein the base used is at least one compound selected from the group consisting of alkali metal and alkaline earth metal hydroxides, alkali metal and alkaline earth metal carbonates, alkali metal hydrogen carbonates, alkali metal and alkaline earth metal acetates, alkal metal and alkaline earth metal alkoxides and primary, secondary and tertiary amines.

5. The process as claimed in claim 4, wherein the base is used in a proportion of 100–500 mol %, based on the aromatic boronic acid.

6. The process as claimed in claim 1, carried out at temperatures between 50° and 150° C.

7. The process as claimed in claim 1, wherein the cross-coupling reaction is carried out in a solvent or solvent mixture which contains at least one compound selected from the group consisting of ethers, hydrocarbons, alcohols, ketones, amides, nitriles and water.

8. The process as claimed in claim 1, wherein the catalyst used is palladium in powdered form, palladium on activated carbon, palladium on aluminum oxide, palladium on barium sulfate or palladium on calcium carbonate, in each case having a palladium content of from 0.5 to 10% by weight.

* * * * *